United States Patent [19]

Okamura

[11] 4,295,092
[45] Oct. 13, 1981

[54] APPARATUS FOR AND METHOD OF DETECTING AND MEASURING CORROSION DAMAGE IN PIPE

[75] Inventor: Okiyoshi Okamura, Mitaka, Japan

[73] Assignee: Koa Oil Company, Limited, Ohte, Japan

[21] Appl. No.: 957,315

[22] Filed: Nov. 3, 1978

[30] Foreign Application Priority Data

Feb. 9, 1978 [JP] Japan .................................. 53-13935
Feb. 9, 1978 [JP] Japan .................................. 53-13936
Feb. 9, 1978 [JP] Japan .................................. 53-13938

[51] Int. Cl.³ ........................ G01R 27/26; G01B 5/28
[52] U.S. Cl. ..................................... 324/61 R; 73/86; 73/105; 324/61 P
[58] Field of Search ................... 324/61 R, 61 P, 220, 324/71 C; 73/86, 105, 432 R; 138/90; 365/102; 179/100.1 B; 361/280

[56] References Cited

U.S. PATENT DOCUMENTS

| 3,361,964 | 1/1968 | Hanson et al. | 324/61 R |
| 3,810,384 | 5/1974 | Evans | 73/623 |
| 3,867,691 | 2/1975 | Plessis | 324/61 R |
| 3,973,441 | 8/1976 | Porter | 73/105 |

FOREIGN PATENT DOCUMENTS

| 61343 | 7/1948 | Netherlands | 324/61 P |
| 1410015 | 10/1975 | United Kingdom | 179/100.1 B |

OTHER PUBLICATIONS

"Stylus Glides . . . "; Electronics; Oct. 26, 1978, pp. 67-68.
Ishikawajima-Harima Engineering Review; Jan. 1978; vol. 18; No. 1; pp. 38-41.

Primary Examiner—Ernest F. Karlsen
Attorney, Agent, or Firm—Thomas L. Giannetti

[57] ABSTRACT

Apparatus for and a method of detecting and measuring the presence and degree of corrosion damage in pipe by using a probe which forms a capacitor with the wall of the pipe is disclosed. The probe is moved interior to and longitudinally of the pipe, and the variation in capacitance occuring whenever the probe passes a corrosion portion of the interior pipe wall is detected.

25 Claims, 10 Drawing Figures

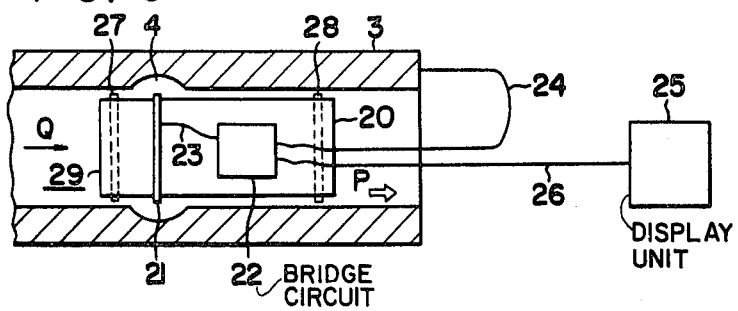
FIG. 5
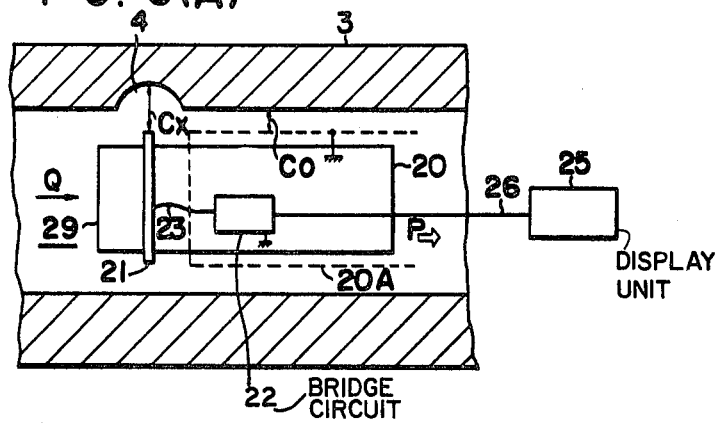
FIG. 6(A)
FIG. 6(B)
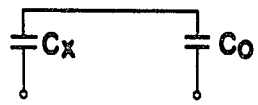
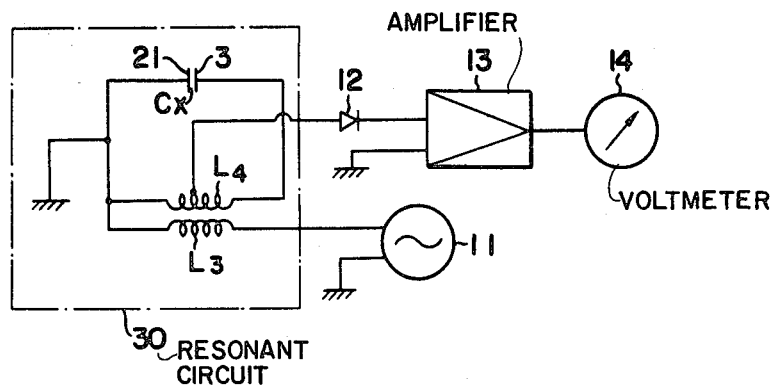
FIG. 7

APPARATUS FOR AND METHOD OF DETECTING AND MEASURING CORROSION DAMAGE IN PIPE

BACKGROUND OF THE INVENTION

This invention relates to a method of and apparatus for detecting the presence of corrosion damage, and more particularly the position and degree of such damage, in hollow pipes or tubes such as those employed in heat exchangers.

In the field of petroleum refining, for example, heat exchangers having a number of pipes or tubes (hereinafter referred to collectively as "pipe") are utilized. This pipe often is exposed to a corrosive atmosphere, making it necessary to inspect them for security and remaining service life.

One method of detecting the degree of corrosion damage in such pipe known as the eddy current type flaw detecting method is extensively employed for austenite stainless steel pipes and brass pipes. This method is described in "Ishikawajima-Harima Engineering Review", Vol. 18, No. 1 (January 1978), pp. 38–41. The eddy current method uses an exciting coil and a detecting coil; flaws in a pipe are detected according to a pulse signal outputted by the detecting coil, or in variations in the impedance thereof. However, the system is disadvantageous in that the output signal does not correspond to the depth of a portion of the pipe damaged by corrosion (hereinafter referred to as "a corrosion portion"). In addition, if the pipe to be inspected is made of a magnetic material, e.g., steel, it must first be magnetically saturated, usually by inserting a coil carrying an electric current into the tubes, which involves considerable difficulty.

A method of measuring the wall thickness of a pipe using radiant rays (e.g., from a radio isotope) is known in the art as the radiograph inspection technique. The radiograph technique is not effective for measuring the degree of corrosion of the inside of the tube. And it is impossible thoroughly to inspect bundled pipe such as might be found in a heat exchanger using the radiograph technique. That is because the measurement of the wall thickness for such pipe can be carried out in one direction only, due to difficulty in positioning the film used in the radiograph technique when the tubes are arranged in close proximity to one another. In addition, fiberscopes have been employed to inspect the inside of pipe, a method which is low in efficiency and which is liable to miss corrosion portions.

In view of the deficiencies of the foregoing, the art has sought other methods more positively and reliably to detect and to measure the degree of corrosion damage in pipe. For instance, destructive sampling inspection in which a typical pipe is removed from the heat exchanger and inspected for damage, from which the corrosion damage to the remaining pipe can be estimated, has been used. However, it is apparent that such a sampling inspection method is based on estimation, is low in efficiency, and is commercially uneconomical. Methods of measuring the wall thickness of a pipe with ultrasonic waves and of directly measuring a flaw with a depth gauge also are known in the art. However, those methods are inefficient and incapable of highly accurate measurement.

Thus the art has sought a method of detecting the degree of corrosion damage which avoids the above-described difficulties accompanying prior methods. In one system, as shown in FIGS. 1 and 2, electrically conductive disks 1 and 2 separated by distance d are disposed perpendicular to the axis of a pipe 3 to be inspected, the circumferential surfaces of the disks being adjacent the inner wall of pipe 3. Pipe 3 has a corrosion portion 4 in its inner wall.

As shown in FIG. 2, disks 1 and 2 can be held by cylinder member 5 made of an insulating material, so that they can be moved longitudinally of the pipe while maintaining constant the distance d between them. For example, as shown in FIG. 1, disks 1 and 2 can be moved in the direction of the arrow from position (I) to position (II) in pipe 3. As shown in FIG. 2, insulating rings 6 and 7, each of which has an outside diameter larger than that of disks 1 and 2 but smaller than the inside diameter of pipe 3, are placed over the two end portions of cylinder member 5; compressed air supplied into pipe 3 moves disks 1 and 2 in the direction of arrow P, for example.

When disks 1 and 2 carry electrical charges opposite in polarity (i.e., one disk charged positively and one disk charged negatively), the lines of electric force between the disks are curved outwardly in the vicinity of the edges of the disks. Moreover, the dielectric constant of the medium through which these outwardly curved lines of force travel differs with the disks located at position (I) in FIG. 1, where there is no damage to pipe 3, from that at position (II), where corrosion portion 4 exists. This difference in dielectric constants occurs due to corrosion portion 4 in the inner wall of the pipe, and as a result the capacitance $C_x$ between disks 1 and 2 is different at position (I) from that at position (II).

The degree of corrosion damage can be detected, as shown in FIG. 3, using bridge circuit 10 formed with disks 1 and 2. A high frequency voltage (144 MHz, for instance) is applied to bridge circuit 10 by high frequency oscillator 11. The resulting unbalanced output voltage of bridge circuit 10 is rectified by rectifying diode 12, and the output of diode 12 is amplified by amplifier 13 and displayed on voltmeter 14. In FIG. 2, reference numeral 15 designates a lead wire or coaxial cable connected to oscillator 11 in FIG. 3, and reference numeral 16 designates a lead wire connected between amplifier 13 (see FIG. 3) and bridge circuit 10 (see FIG. 3), which may be built into the probe.

The values of reference capacitor $C_s$ and reference inductance coils $L_1$ and $L_2$ of bridge circuit 10 are selected such that the output of bridge 10 is at a minimum when the disks are not adjacent a corrosion portion, e.g., at the position (I) in FIG. 1. Thus, when disks 1 and 2 are moved to position (II), adjacent corrosion portion 4, the value of the static capacitance $C_x$ of the disks is changed as described above, increasing the unbalanced output of bridge circuit 10. The degree of variation of that output corresponds to the degree of corrosion damage. Using an analytical curve, e.g., a curve determined in advance from reference pipes relating readings of voltmeter 14 to the degree of corrosion damage, the degree of corrosion damage can be measured.

FIG. 4 shows another detecting device known to the art. Inductance coil 17 is provided instead of the capacitance between the disks in FIGS. 1-3. The magnetic lines of flux emanating from inductance coil 17 link the walls of pipe 3, which walls vary in magnetic permeability due to the presence of corrosion portion 4. In this case, the degree of corrosion damage is detected by the change in coil inductance caused by variations in the magnetic permeability of the pipe walls. Coil 17 is part of bridge circuit 10, analogous to bridge circuit 10 described above in connection with FIGS. 1–3 and shown diagrammatically in FIG. 3.

SUMMARY OF THE INVENTION

It is thus an object of this invention to provide a method of and apparatus for detecting the presence, position, and degree of corrosion damage in the inner wall of a hollow pipe which are simple, efficient, reliable, and commercially economical.

It is another object of this invention to provide an improved method of and apparatus for detecting the presence, position, and degree of corrosion damage in electrically conductive pipe which do not require magnetic saturation of the pipe.

It is still another object of this invention to provide an improved method of and apparatus for detecting the presence, position, and degree of corrosion damage in pipe which are suitable for use with bundled pipe such as is commonly used in heat exchangers.

It is a further object of this invention to provide an improved method of and apparatus for detecting the presence, position, and degree of corrosion damage in pipe which do not require destructive sampling of the pipe.

It is a further object of this invention to provide a method of and apparatus for detecting the presence, position, and degree of corrosion damage in pipe which can accurately detect the degree of locally formed corrosion, e.g., pitting, of the pipe wall.

And it is still a further object of this invention to provide a probe for use in a method of and apparatus for detecting the presence, position, and degree of corrosion damage in pipe in which the electrical wiring is simplified.

In accordance with a preferred embodiment of the present invention, there is provided a method of and apparatus for detecting the degree of corrosion damage in electrically conductive pipe comprising varying electrical capacitance means comprising a movable conductive member within said pipe, and means for moving the conductive member longitudinally of the pipe. The conductive member and the pipe wall form the electrodes of the varying electrical capacitance means such that the capacitance of the varying capacitance means changes whenever the movable conductive member passes a corrosion portion of the inner pipe wall. This method and apparatus further comprise means electrically connected to the varying capacitance means for detecting the variations in its electrical capacitance. This embodiment of the present invention is advantageous in that a second conductive member within the pipe used as the second electrode of a varying electrical capacitance in prior detection methods and apparatus is not needed, thus simplifying the detecting apparatus and method.

Another preferred embodiment of the present invention is a method of apparatus for detecting the degree of corrosion damage in electrically conductive pipe comprising first varying electrical capacitance means comprising a plurality of conductive members; non-conductive means for carrying the plurality of conductive members and means interacting with the carrying means for moving the plurality of conductive member longitudinally of the pipe. The carrier means and plurality of conductive members are located interior to the pipe and are movable longitudinally of the pipe. The conductive members are positioned substantially symmetrically and substantially uniformly over the outer surface of the carrier means. Each conductive member and the wall of the pipe form the electrodes of a varying electrical capacitor such that the capacitance of each such varying capacitor changes whenever the associated conductive member passes a corrosion portion of the inner pipe wall. The apparatus and method further comprise first detecting means electrically connected to the first varying capacitance means for detecting the variations in its electrical capacitance. This preferred embodiment is advantageous for measuring the degree of locally formed corrosion, e.g., pitting, of the inner pipe wall, which may not be accurately measurable with other detection methods and apparatus, for example, those using a single varying capacitance. The detected variations may be displayed by display means electrically connected to the detecting means.

This embodiment of the present invention may further comprise second varying capacitance means comprising a movable conductive member substantially encircling a portion of the carrier means, forming a capacitor with the wall of the pipe; second detecting means electrically connected to the second varying capacitance means for detecting the variations in its capacitance; and second display means electrically connected to the second detecting means for displaying the detected variations in capacitance of the second varying capacitance means. With this preferred embodiment of the present invention both uniform corrosion and locally formed corrosion can be detected and measured.

Another preferred embodiment of the present invention is a probe for detecting corrosion damage to electrically conductive pipe. The probe comprises a non-conductive cylindrical member having an outside diameter less than the inside diameter of the pipe and being adapted and constructed to be movable within the pipe longitudinally of the pipe; a pair of insulating rings, one encircling each end of the cylindrical member, the outside diameter of each ring being slightly less than the inside diameter of the pipe; and a single conductive member encircling the cylindrical member between the insulating rings, the outside diameter of the conductive member being less than that of the insulating rings. The conductive member is arranged and adapted to form with the wall of the pipe a varying electrical capacitance whose capacitance changes whenever the conductive member passes a corrosion portion of the inner pipe wall as the cylindrical member is moved within the pipe longitudinally of the pipe. Detecting means electrically connected to varying capacitance means for detecting the variations in its capacitance are built into the cylindrical member of the probe in another preferred embodiment of the present invention.

The foregoing and further objects of the present invention will become apparent from the detailed description of the invention and accompanying drawings, in which like parts are designated by like reference numerals or characters.

DESCRIPTION OF THE DRAWINGS

FIG. 5 shows one device for detecting the degree of corrosion damage according to this invention;

FIG. 6(A) shows another device for detecting the degree of corrosion damage according to this invention;

FIG. 6(B) is an equivalent circuit of the device shown in FIG. 6(A);

FIG. 7 is a schematic circuit diagram (partly as a block diagram) showing one example of a detecting circuit employed in this invention;

DETAILED DESCRIPTION OF THE INVENTION

Figure 3:
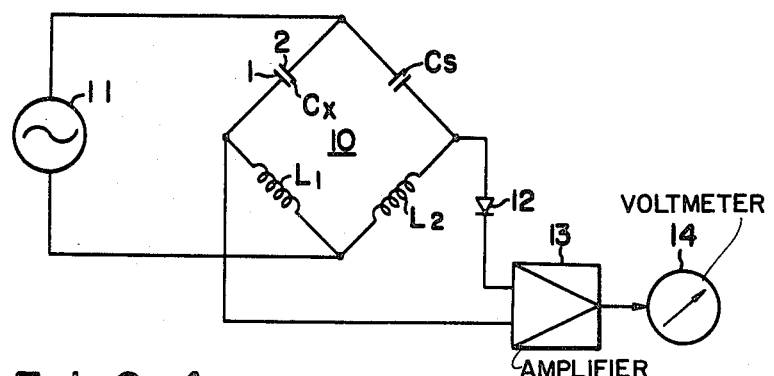
FIG. 3 is a diagram of a conventional detecting circuit.

Referring to FIG. 5, reference numeral 20 designates a cylinder member made of an insulating material and having an outside diameter smaller than the inside diameter of a pipe 3; reference numeral 21, a ring made of an electrically conductive material and fixedly secured around the outer wall of cylinder member 20; and reference numeral 22, a bridge circuit as shown in FIG. 3 which is preferably molded into cylinder member 20. In place of bridge circuit 22, a resonance circuit such as that shown in FIG. 7 may be employed in a manner described below in detail. Returning to FIG. 5, reference numeral 24 designates a lead wire connecting bridge circuit 22 to pipe 3; reference numeral 23, a lead wire connecting bridge circuit 22 to ring 21; and reference numeral 25, a display unit provided external to pipe 3. Display unit 25 comprises amplifier 13 and voltmeter 14 described above in connection with FIG. 3. Display unit 25 is connected through lead wires 26 to bridge circuit 22. A rectifying diode (not shown) is connected to lead wire 26 in cylinder member 20.

In this detection system, the capacitance between the inner wall of pipe 3 and ring 21 is employed as capacitor $C_x$ in FIG. 3, and changes in this electrostatic capacitance are sensed to detect a corrosion portion 4 of the pipe.

Rings 27 and 28 are provided at the end portions of cylinder member 20 as shown in FIG. 5 to form detecting probe 29. Each of rings 27 and 28 has an outside diameter larger than that of ring 21 but slightly smaller than the inside diameter of pipe 3, and each ring is made of an insulating material.

In this system, compressed air is supplied to the interior of the pipe in the direction of arrow Q to move detecting probe 29 longitudinally of the pipe in the direction of arrow P. When electrically conductive ring 21 is at a position in the pipe where no corrosion damage exists, the capacitance between the pipe 3 and ring 21 is constant. However, when ring 21 passes adjacent a corrosion portion, e.g., corrosion portion 4 of pipe 3, as shown in FIG. 5, the capacitance between ring 21 and pipe 3 is decreased as the distance therebetween is increased.

Pipe 3 and ring 21 are employed, respectively, as electrodes 1 and 2 forming one arm of bridge circuit 10 (FIG. 3). The degree of corrosion damage can be detected in accordance with the above-described principles. That is, if the relationship (e.g., an analytical curve) between the degree of corrosion damage and the output voltage of bridge circuit 22 is known, then the degree of corrosion damage can be measured from display unit 25 (e.g., by reading the voltmeter which is part of that unit). Thus, the arrangement of the detecting element is simplified by detecting the capacitance between pipe 3 and ring 21 in a manner described.

In practice, it is not necessary to connect the pipe 3 to bridge circuit 22 with lead wire 24, in the manner shown in FIG. 5. If a portion of cylinder member 20 (not inlcluding ring 21) is covered by shielding material 20A (see FIG. 6(A)), then a constant "stray" capacitance $C_o$ is provided between shielding material 20A and pipe 3. As a result, a series circuit connection of capacitors $C_x$ and $C_o$ having an effective value of capacitance C $[(C=C_oC_x/(C_o+C_x)]$ is formed, as shown in FIG. 6(B). Using this series circuit containing capacitors $C_o$ and $C_x$ as one arm of bridge circuit 22, the degree of corrosion damage can be measured using the above-described method.

Alternatively, a resonant circuit including the capacitor formed by ring 21 and pipe 3 can be used instead of the abovedescribed bridge circuit 22. An example of such a resonant circuit is designated by reference numeral 30 in FIG. 7, in which reference character $L_3$ designates a primary coil connected to high frequency oscillator 11, and reference character $L_4$ designates a secondary coil which is electromagnetically coupled to primary coil $L_3$. Resonant circuit 30 is made up of coils $L_3$ and $L_4$ and the aforementioned capacitor $C_x$ including ring 21 and pipe 3. The resonance voltage is picked up from the center tap of secondary coil $L_4$, rectified by diode 12, and applied through amplifier 13 to voltmeter 14, where it is displayed.

Resonant circuit 30 and diode 12 are preferably incorporated in cylinder member 20. If oscillator 11 is fabricated in the form of an integrated circuit, it too can be built into cylinder member 20. In the latter case, it is sufficient to use multi-core cable as the lead wire extended into pipe 3, to connect oscillator 11 to a DC current source (not shown) and to transmit the output signal from the probe. With oscillator 11 not built into cylinder member 20, for stability a coaxial cable is used as a lead wire extended into pipe 3.

Figure 1:
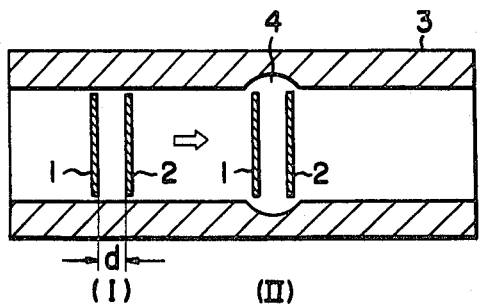
FIGS. 1 and 2 show a conventional system of detecting the degree of corrosion damage in pipe.
Figure 2:
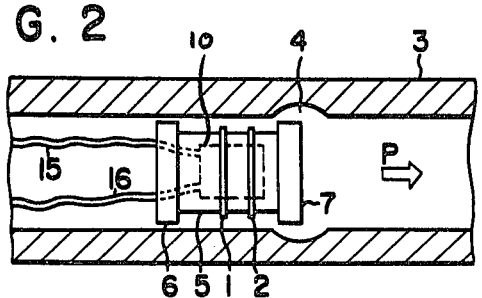

If resonant circuit 30 is so adjusted that the maximum resonance voltage is obtained when detecting probe 29 is at position (I) in FIG. 1, when the probe is at position (II), where the pipe is corroded, the resonance relation is disestablished because of the variation of capacitance $C_x$ caused by the corrosion portion. As a result, the output voltage of the resonant circuit is descreased by an amount corresponding to the degree of corrosion damage. By measuring this output voltage decrease, the degree of corrosion damage can be measured, e.g., using an analytical curve.

Figure 4:
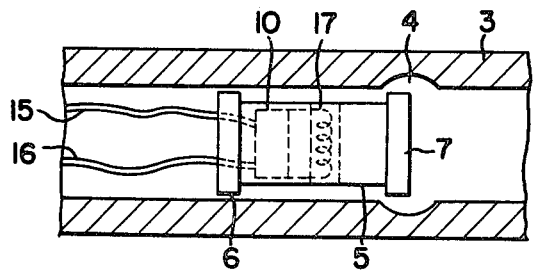
FIG. 4 shows another conventional device for detecting the degree of corrosion damage in pipe.

It will be appreciated that the use of a resonant circuit in place of a bridge circuit is not limited to the apparatus for detecting corrosion damage described in connection with FIG. 5. For example, in the apparatus described above in connection with FIG. 4, a resonant circuit containing inductance coil 17 as one element could be substituted for bridge circuit 10.

In the probe described above, a single ring 21 is provided surrounding the outer wall of cylinder member 20 forming the detecting probe. Although the single ring configuration will provide accurate measurements of corrosion depth for general or uniform corrosion, where the corrosion depth is substantially constant around the circumference of the interior pipe wall, that arrangement may not accurately detect the depth of corrosion for corrosion portions which are locally formed. Locally formed corrosion is a type of corrosion which is nonuniform in depth around the circumference of the interior pipe wall. An example of locally formed corrosion whose depth may not be accurately measured using a probe with a single ring 21 is pitting. That is because the variation of the electrostatic capacitance $C_x$ due to corrosion may be the same for a pitted corrosion portion which is narrow and deep as for a pitted corrosion portion which is wide and shallow. For both cases, the output voltage of amplifier 13 could be the same and the different depths of the defects could therefore not be detected.

Figure 8:
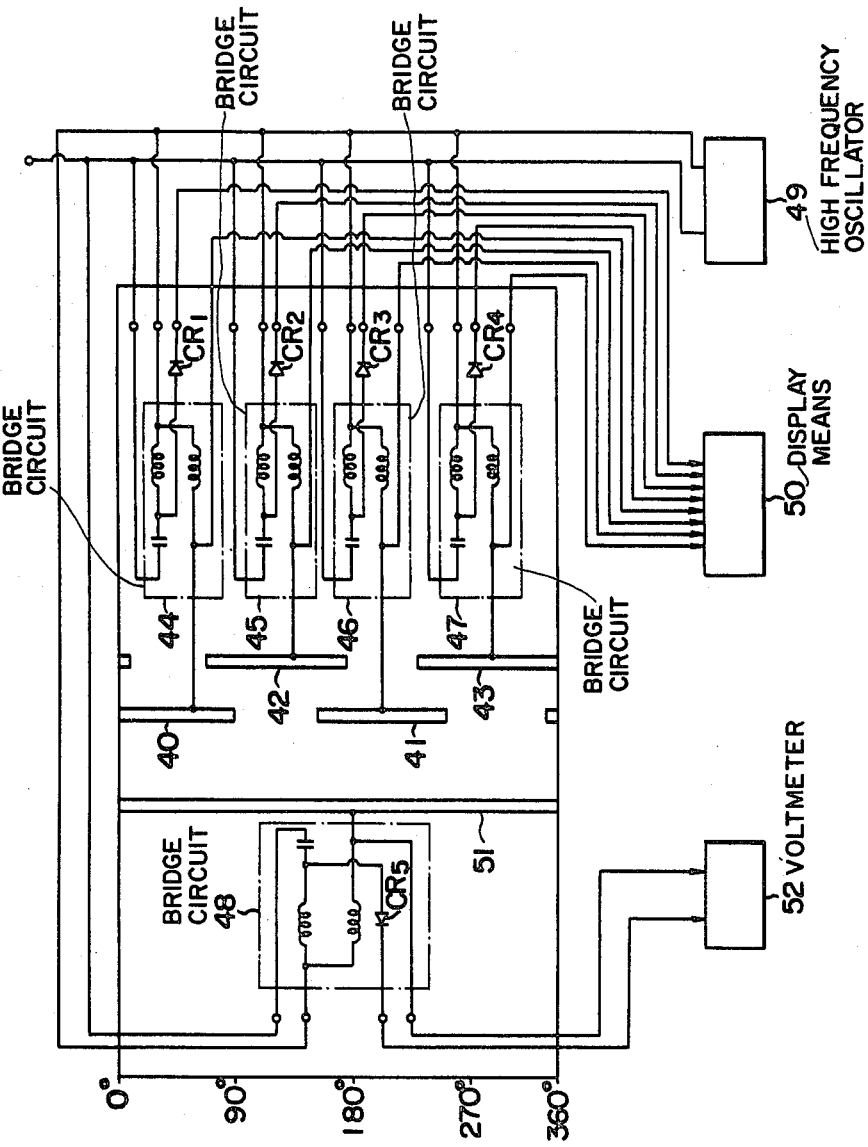
FIG. 8 is a schematic circuit diagram showing an alternative embodiment of the device to this invention.

This difficultly can be eliminated by providing, as shown in FIG. 8, a plurality of electrically conductive members 40 through 43 uniformly and symmetrically positioned over the entire surface of the cylinder member, and by further providing bridge circuits 44 through 47, one connected to each of electrically conductive members 40 through 43. Each of bridge circuits 44 through 47 is shielded and independent from the others, and is connected to high frequency oscillator 49, which is like oscillator 11 described above in connection with FIG. 3. The outputs of the bridge circuits 44 through 47 are converted into DC signals by means of diodes $CR_1$ through $CR_4$, respectively, each DC signal being displayed by display means 50 comprising a plurality of voltmeters, one connected to each bridge circuit. With this device, local corrosion damage in the pipe can be positively detected. Of course, it will be appreciated that accuracy in detecting the depth of locally formed corrosion portions can be improved by providing additional conductive members over the surface of the cylinder member beyond the four such members shown in FIG. 8, and additional bridge circuits and diodes associated with those conductive members.

If ring 51, bridge circuit 48 connected to oscillator 49, and rectifying diode $CR_5$, which are similar in operation to those previously described in connection with FIG. 5, are provided in addition to the plurality of electrical conductive members 40 through 43 and the plurality of bridge circuits 44 through 47, the location of corrosion damage can be detected, as well, by voltmeter 52.

Figure 9:
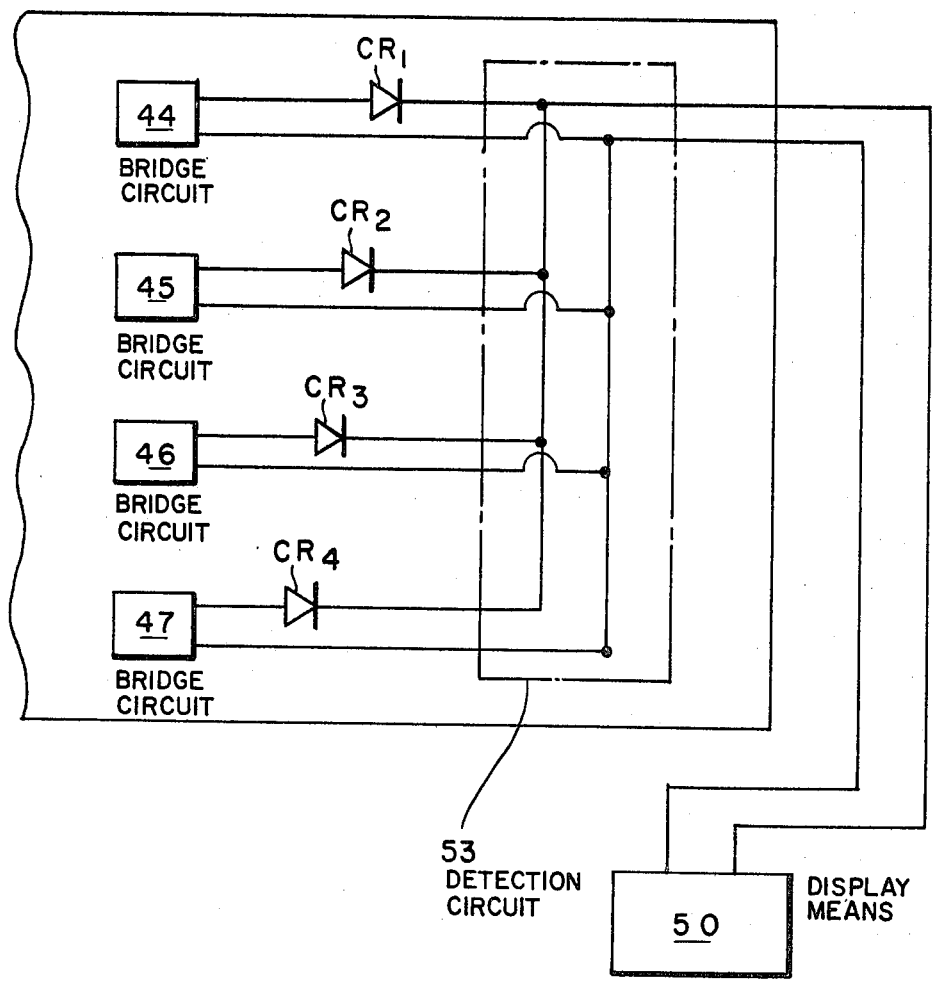
FIG. 9 is a schematic circuit diagram showing another alternative embodiment of the device according to this invention.

In the example shown in FIG. 8, the output of each bridge circuit is detected by a respective voltmeter which is part of display means 50. In practice, however, it is normally sufficient to measure only the maximum depth of the corrosion portion, which can be accomplished by detecting the highest of the outputs of bridge circuits 44 through 47. In that case, the outputs of bridge circuts 44 through 47 are rectified into DC signals, which are applied as shown in FIG. 9 to a logical "OR" circuit connection 53 detecting the highest voltage. That voltage is then indicated on a display means 50 comprisng a single voltmeter, which may for convenience be connected to a recorder (not shown) which records the voltage readings.

The reading of voltmeter 52, which it will be recalled may not accurately measure the depth of local corrosion (e.g., pitting), but is capable of accurately measuring general corrosion, can be compared to the reading on voltmeter 50. By comparing the reading of voltmeter 52 to the reading on voltmeter 50, it can be determined if general corrosion has occured (if both voltmeters 52 and 50 show the same reading or if the reading on voltmeter 52 is greater than the reading on voltmeter 50), or if local corrosion has occured (if the reading on voltmeter 52 is less than the reading on voltmeter 50). If general corrosion is indicated by comparing the meter readings, the reading on voltmeter 52 is adopted as showing the depth of the general corrosion portion. If local corrosion is indicated by comparing the meter readings, the reading on voltmeter 50 is adopted as showing the maximum depth of the local corrosion portion.

It has been found that wiring of the probe can be simplified when the outputs of bridge circuits 44 through 47 are rectified by diodes $CR_1$ through $CR_4$, respectively, as shown in FIG. 8. That is because with rectification coaxial cable need not be used to connect the probe to voltmeter 50. Further simplfication of the wiring of the probe is achieved by using the logical "OR" detection circuit 53 shown in FIG. 9 and described above. For that configuration, a shielded dual-core cable can be used to electrically connect the probe to display means 50.

I claim:

1. Apparatus for detecting corrosion damage to electrically conductive pipe, comprising:
   (a) a movable conductive ring within said pipe; and
   (b) means for moving said conductive ring longitudinally of said pipe;
       said conductive ring and the wall of said pipe forming the electrodes of a varying electrical capacitance means such that the capacitance of said varying capacitance means changes whenever said movable conductive ring passes a corrosion portion of the inner pipe wall; and
   (c) means electrically connected to said varying capacitance means for detecting the variations in its electrical capacitance.

2. The apparatus of claim 1, further comprising:
   (d) means electrically connected to said detecting means for displaying the detected variations in the capacitance of said varying electrical capacitance means.

3. The apparatus of claim 2, wherein said detecting means comprises an electrical bridge circuit having a plurality of arms and exciting means electrically connected to said bridge circuit, said varying capacitance means forming one arm of said bridge circuit, said bridge circuit being constructed such that its unbalanced output changes whenever said movable conductive ring passes a corrosion portion of the inner pipe wall.

4. The apparatus of claim 2, wherein said detecting means comprises an electrical resonant circuit and exciting means electrically connected to said resonant circuit, said resonant circuit being adjusted such that resonance is established whenever said movable conductive ring is not passing a corrosion portion of the inner pipe wall and resonance is disestablished whenever said movable conductive ring passes a corrosion portion of the inner pipe wall.

5. The apparatus of claim 2, further comprising:
   (e) constant electrical capacitance means circuit connected to said variable capacitance means, said circuit connected combination of constant and varying capacitance means being electrically connected to said detecting means.

6. The apparatus of claim 2, further comprising:
   (e) means electrically connected between said detecting means and said display means for rectifying the output of said detecting means before said output is displayed by said display means.

7. Apparatus for detecting corrosion damage to electrically conductive pipe, comprising:
   (a) a plurality of conductive members;

(b) non-conductive means for carrying said plurality of conductive members, said carrier means and said conductive members being located interior to and being movable longitudinally of said pipe, said conductive members being positioned substantially symmetrically and substantially uniformly over the outer surface of said carrier means; and (c) means interacting with said carrier means for moving said plurality of conductive members longitudinally of said pipe;

each said conductive member and the wall of said pipe forming the electrodes of a varying electrical capacitor such that the capacitance of each said varying capacitor changes whenever the associated conductive member of said plurality of conductive member passes a corrosion portion of the inner pipe wall;

(d) a first varying capacitance means comprised of said varying electrical capacitors formed by said plurality of conductive members and the pipe wall; and (e) first detecting means electrically connected to said first varying capacitance means for detecting the variations in its electrical capacitance.

8. The apparatus of claim 7, further comprising:

(f) first display means electrically connected to said first detecting means for displaying the detected variations in the capacitance of said first varying electrical capacitance means.

9. The apparatus of claim 8, wherein said first detecting means further comprises means for detecting the maximum variation in the capacitance of the varying electrical capacitors of said first varying electrical capacitance means formed by each said of said plurality of conductive members and said pipe, and wherein said first display means further comprises means for displaying said maximum variation in capacitance.

10. The apparatus of claim 9, wherein said means for detecting the maximum variation in capacitance of the individual electrical capacitors of said first varying electrical capacitance means comprises a logical "OR" circuit.

11. The apparatus of claim 8, further comprising:

(g) a second movable conductive member interior to said pipe affixed to and substantially encircling a portion of said carrier means, said conductive member and the wall of said pipe forming the electrodes of a second varying electrical capacitance means such that the capacitance of said varying capacitance means changes whenever said conductive member substantially encircling a portion of said carrier means passes a corrosion portion of the inner pipe wall;

(h) second detecting means electrically connected to said second varying capacitance means for detecting the variations in its electrical capacitance; and (i) second display means electrically connected to said second detecting means for displaying the detected variations in the capacitance of said second varying electrical capacitance means.

12. A method for detecting corrosion damage to electrically conductive pipe, comprising:

(a) forming a varying electrical capacitor using the pipe as an electrode of said capacitor and a conductive ring movable within said pipe as another electrode of said capacitor;

(b) moving said conductive member interior to and longitudinally of said pipe; and (c) detecting with electrical circuit means the variations in the capacitance of said varying electrical capacitor occurring whenever said moving conductive member passes a corrosion portion interior to said pipe.

13. The method of claim 12, further comprising:

(d) displaying the detected variations in the capacitance of said varying capacitor.

14. A method for detecting corrosion damage to electrically conductive pipe, comprising:

(a) forming a plurality of first varying electrical capacitors using the pipe as one electrode of each of said plurality of first capacitors, and one of a plurality of first movable conductive members in said pipe as another electrode of each of said plurality of first capacitors; said plurality of first conductive members being substantially uniformly and substantially symmetrically positioned over the surface of an insulating cylindrical member in the pipe;

(b) moving said plurality of first conductive members and said cylindrical member longitudinally of the pipe; and (c) detecting with electrical circuit means the changes in the capacitance of said first varying capacitors.

15. The method of claim 14, wherein the detecting of the variations in the capacitance of said first varying capacitors further comprises detecting the maximum variation in the capacitance of said first varying capacitors.

16. The method of claim 14, further comprising:

(d) displaying the detected variations in the capacitance of said first varying capacitors.

17. The method of claim 16, further comprising:

forming a second varying electrical capacitor using the pipe as one electrode and a second movable conductive member in the pipe substantially encircling said insulating cylindrical member in the pipe as another electrode of said second varying capacitor; wherein the moving of said plurality of first conductive members and said cylindrical member longitudinally of the pipe further comprises moving said second conductive member longitudinally of the pipe; wherein the detecting of the changes in the capacitance of said first varying capacitors further comprises detecting the changes in the capacitance of said second varying capacitor; and wherein the displaying of the detected variations in the capacitance of said first varying capacitors further comprises displaying the detected variations in the capacitance of said second varying capacitor.

18. A probe for detecting corrosion damage to electrically conductive pipe, comprising:

(a) a non-conductive cylindrical member having an outside diameter less than that of the inside diameter of the pipe, said cylindrical member being adapted and constructed to be movable within said pipe longitudinally of the pipe;

(b) a pair of insulating rings, one encircling each end of said cylindrical member, the outside diameter of each said ring being slightly less than the inside diameter of said pipe; and (c) a first conductive member substantially encircling said cylindrical member between said insulating rings, the outside diameter of said first conductive member being less than that of said insulating rings, said first conductive member being arranged and adapted to form with the wall of said pipe the electrodes of a first varying electrical capacitance whose capacitance changes whenever said first conductive member passes a corrosion portion of the inner pipe wall as said cylindrical member is moved within said pipe longitudinally of the pipe.

19. The probe of claim 18, further comprising:
(d) a conductive shielding member encircling a substantial portion of said cylindrical member not including said first conductive member, said shielding member forming with said pipe the electrodes of a constant electrical capacitance electrically circuit connected to said first varying capacitance formed by said first conductive member and said pipe.

20. The probe of claim 18, further comprising:
(d) first detecting means electrically connected to said first varying capacitance means for detecting variations in the capacitance of said first varying capacitance means, said detecting means being built into said cylindrical member.

21. The probe of claim 20, further comprising:
(e) a plurality of second conductive members substantially uniformly and substantially symmetrically positioned over the surface of said cylindrical member, each of said second conductive members forming with said pipe the electrodes of one of a plurality of second varying capacitances, the capacitance of each of said plurality of second varying capacitances changing whenever the associated second conductive member passes a corrosion portion of the inner pipe wall as said cylindrical member is moved within said pipe longitudinally of the pipe; and
(f) second detecting means for detecting variations in the capacitance of said plurality of second varying capacitances, said second detecting means being built into said cylindrical member.

22. The probe of claim 21, wherein said second detecting means built into said cylindrical member further comprises means for detecting the maximum variation in the capacitances of said plurality of second varying capacitances.

23. The probe of claim 22, wherein said means built into the cylinder member for detecting the maximum variation in the capacitances of said second varying capacitances comprises a logical "OR" circuit.

24. Apparatus for detecting the presence and degree of corrosion damage to electrically conductive pipe, comprising:
(a) a first conductive member movable within said pipe;
(b) means for moving said conductive member within said pipe, longitudinally of the pipe;
(c) electrical means circuit connected between said first conductive member and said pipe for establishing an electric field between said first conductive member and the walls of said pipe, the lines of force of said electric field impinging on a substantial portion of the inner circumference of said pipe wall; said conductive member, said electrical circuit means and said pipe forming a first varying electrical capacitance such that the capacitance of said first varying capacitance changes when said first movable conductor passes a corrosion portion of said inner pipe wall; and
(d) first detecting means electrically connected to said first varying capacitance for detecting the changes in its electrical capacitance.

25. The apparatus of claim 24, further comprising:
(e) a plurality of second conductive members adapted to be located interior to and moved longitudinally of said pipe;
(f) means for moving said plurality of second conductive members within said pipe, longitudinally of the pipe, simultaneously with the moving of said first conductive member longitudinally of said pipe;
(g) electrical means circuit connected between said plurality of second conductive members and said pipe for establishing an electric field between each of said conductive members and the walls of said pipe, the lines of force of said electrical field associated with each conductive member of said plurality of second conductive members impinging on a segment of the inner circumference of said pipe wall; said plurality of second conductive members, said electrical circuit means and said pipe forming a plurality of second varying capacitances such that the capacitance of each such varying capacitance changes when the associated conductive member of the plurality of second conductive members passes a corrosion portion of the inner pipe wall; and
(h) second detecting means electrically connected to said plurality of second varying capacitances to detect the changes in its electrical capacitance.

* * * * *